US009205005B2

(12) United States Patent
Kikuchi et al.

(10) Patent No.: US 9,205,005 B2
(45) Date of Patent: Dec. 8, 2015

(54) ABSORBENT ARTICLE AND DISPOSABLE DIAPER HAVING VIEWED-THROUGH TOP SHEET

(75) Inventors: Kyo Kikuchi, Kanonji (JP); Kei Wakasugi, Kanonji (JP); Junko Ueda, Kanonji (JP); Naoto Ohashi, Kanonji (JP); Yasuhiro Yamanaka, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 302 days.

(21) Appl. No.: 13/824,191

(22) PCT Filed: Sep. 26, 2011

(86) PCT No.: PCT/JP2011/072703
§ 371 (c)(1),
(2), (4) Date: Mar. 15, 2013

(87) PCT Pub. No.: WO2012/043842
PCT Pub. Date: Apr. 5, 2012

(65) Prior Publication Data
US 2013/0178811 A1 Jul. 11, 2013

(30) Foreign Application Priority Data
Sep. 30, 2010 (JP) ................. 2010-223309

(51) Int. Cl.
*A61F 13/15* (2006.01)
*A61F 13/20* (2006.01)
(Continued)

(52) U.S. Cl.
CPC .......... *A61F 13/51394* (2013.01); *A61F 13/49* (2013.01); *A61F 13/51104* (2013.01); *A61F 2013/15243* (2013.01); *A61F 2013/51377* (2013.01); *A61F 2013/8497* (2013.01)

(58) Field of Classification Search
CPC .............. A61F 13/51394; A61F 13/51104; A61F 2013/51361; A61F 2013/51383; A61F 2013/51388
USPC ................. 604/385.01, 367, 362, 360, 375
See application file for complete search history.

(56) References Cited

U.S. PATENT DOCUMENTS 3,929,135 A * 12/1975 Thompson ............... 604/385.08
4,324,246 A * 4/1982 Mullane et al. ............. 604/366
(Continued)

FOREIGN PATENT DOCUMENTS

EP 0951889 A1 10/1999
JP 11299825 A 11/1999
(Continued)

OTHER PUBLICATIONS

International Search Report dated Jan. 31, 2013, issued in PCT/JP2011/072703, 2 pages.

Primary Examiner — Michelle M Kidwell
(74) Attorney, Agent, or Firm — Hauptman Ham, LLP

(57) ABSTRACT

An absorbent article has a liquid-permeable top sheet of a white non-woven fabric, a liquid-impermeable back sheet opposing the top sheet, and an absorbent between the top sheet and the back sheet. A colored element is provided on the side of the top sheet that does not contact the skin, is visible through the top sheet, and is colored to a color other than white. The top sheet has protrusions and indentations in the thickness direction. The basic weight of the protrusions is greater than the basic weight of the indentations. The color difference between the Lab value of the color of the colored element visible through the protrusions of the top sheet and the Lab value of the color of the colored element visible through the indentations of the top sheet is 2.8 or more.

21 Claims, 7 Drawing Sheets

(51) Int. Cl.
*A61F 13/513* (2006.01)
*A61F 13/49* (2006.01)
*A61F 13/511* (2006.01)
*A61F 13/84* (2006.01)

(56) References Cited

U.S. PATENT DOCUMENTS

| | | | | |
|---|---|---|---|---|
| 4,324,314 | A * | 4/1982 | Beach et al. | 181/230 |
| 4,463,045 | A * | 7/1984 | Ahr et al. | 428/131 |
| 4,609,518 | A * | 9/1986 | Curro et al. | 264/504 |
| 4,629,643 | A * | 12/1986 | Curro et al. | 428/131 |
| 5,006,394 | A * | 4/1991 | Baird | 428/138 |
| 7,429,689 | B2 * | 9/2008 | Chen et al. | 604/378 |
| 8,251,965 | B2 * | 8/2012 | Costea et al. | 604/385.01 |
| 2002/0062115 | A1 | 5/2002 | Wada et al. | |
| 2007/0298671 | A1 | 12/2007 | Noda et al. | |
| 2011/0060301 | A1 | 3/2011 | Nishikawa et al. | |
| 2013/0281950 | A1 * | 10/2013 | Digiacomantonio et al. | 604/366 |

FOREIGN PATENT DOCUMENTS

| | | |
|---|---|---|
| JP | 20048592 A | 1/2004 |
| JP | 2005-512682 A | 5/2005 |
| JP | 2009-173 A | 1/2009 |
| JP | 2009173 A | 1/2009 |
| JP | 2009-207684 A | 9/2009 |
| JP | 2009207684 A | 9/2009 |
| WO | 03053313 A2 | 7/2003 |

* cited by examiner (a)

(b)

(a)

(b)

(a)

(b)

(a)

(b)

(a)

(b)

(a)

(b)

(a)

(b)

ABSORBENT ARTICLE AND DISPOSABLE DIAPER HAVING VIEWED-THROUGH TOP SHEET

RELATED APPLICATIONS

The present application is a National Phase of International Application Number PCT/JP2011/072703, filed Sep. 26, 2011, and claims priority from Japanese Application Number 2010-223309, filed Sep. 30, 2010.

TECHNICAL FIELD

The present invention (disclosure) relates to an absorbent article and a disposable diaper.

BACKGROUND ART

An absorbent article is known in the prior art in which a colored portion is provided in an insert arranged between a top sheet and an absorbent core in order to convey the existence of enhanced function of the absorbent article to consumers (see, for example, Patent Document 1). In this absorbent article, the colored portion has at least a first color tone and a second color tone, and by displaying the second color tone within an area of the first color tone, sensory perception of depth can be created within the absorbent article.

CITATION LIST

Patent Literature

[Patent Literature 1] PCT Application No. WO2003/053313

SUMMARY OF THE INVENTION

Technical Problem

In the above-described absorbent article, the inventor(s) has recognized that when a characteristic is to imparted to the surface of the side of the top sheet of the absorbent article that contacts the skin, it might be difficult to form a colored portion having at least two color tones to match that surface form. In addition, since it might not be possible to form a colored portion having at least two color tones that matched the surface form for the colored portion, a user might have the impression of a surface form that differs from the actual surface form of the side of the top sheet of the absorbent article that contacts the skin imparted to a user.

Solution to Problem

In a first aspect, an absorbent article is provided with a liquid-permeable top sheet composed of a white non-woven fabric, a liquid-impermeable back sheet provided at a location opposing the top sheet, and an absorbent provided between the top sheet and the back sheet, wherein a colored element is further provided on the side of the top sheet that does not contact the skin that is visible through the top sheet and is colored to a color other than white, the top sheet has a plurality of protrusions protruding in the thickness direction and a plurality of indentations indented in the thickness direction, the basic weight of the protrusions is greater than the basic weight of the indentations, and the color difference between the Lab value of the color of the colored element visible through the protrusions of the top sheet and the Lab value of the color of the colored element visible through the indentations of the top sheet is 2.8 or more.

A disposable diaper of the present invention displays a striped pattern that extends in the same direction as the direction in which the protrusions and indentations of the top sheet extend in an area in the center in the widthwise direction of the top sheet that surrounds the torso, the striped pattern is the same color as the color of the colored element, and the striped pattern is displayed by providing an elastic material colored to a color other than white on the surface that does not contact the skin of the area in the center in the widthwise direction of the top sheet that surrounds the torso.

In another disposable diaper of the present invention is a disposable diaper provided with a liquid-permeable top sheet composed of a white non-woven fabric, a liquid-impermeable back sheet provided at a location opposing the top sheet, and an absorbent provided between the top sheet and the back sheet, wherein a second sheet colored to a color other than white is further provided between the top sheet and the absorbent, the top sheet has a plurality of protrusions protruding in the thickness direction and a plurality of indentations indented in the thickness direction, the basic weight of the protrusions is greater than the basic weight of the indentations, the second sheet is provided in a portion of an area in the planar direction of the absorbent, the color difference between the Lab value of the color of the second sheet visible through the protrusions of the top sheet and the Lab value of the color of the second sheet visible through the indentations of the top sheet is 2.8 or more, and the area in the planar direction where the second sheet is provided differs between a disposable diaper for use by men and that for use by women.

Advantageous Effects of the Invention

According to the present invention, surface irregularities (undulations) in the form of protrusions and indentations on the side of a top sheet of an absorbent article that contacts the skin can be accurately emphasized.

DESCRIPTION OF EMBODIMENTS

First Embodiment

The following provides an explanation of an absorbent article of a first embodiment of the present invention with reference to the drawings. The absorbent article of the first embodiment of the present invention is a disposable diaper, however, as will be readily appreciated by those skilled in the art, the absorbent article need not be limited to a disposable diaper. The top sheet of nonwoven fabric and the colored element of the first embodiment and of any of the described embodiments may be taken in isolation of the disclosed diapers and applied to alternative absorbent articles that also feature a backsheet and an absorbent, for example, alternative known diaper constructions, sanitary napkins, etc. The disclosed absorbent articles represent exemplary embodiments only.

Figure 1:
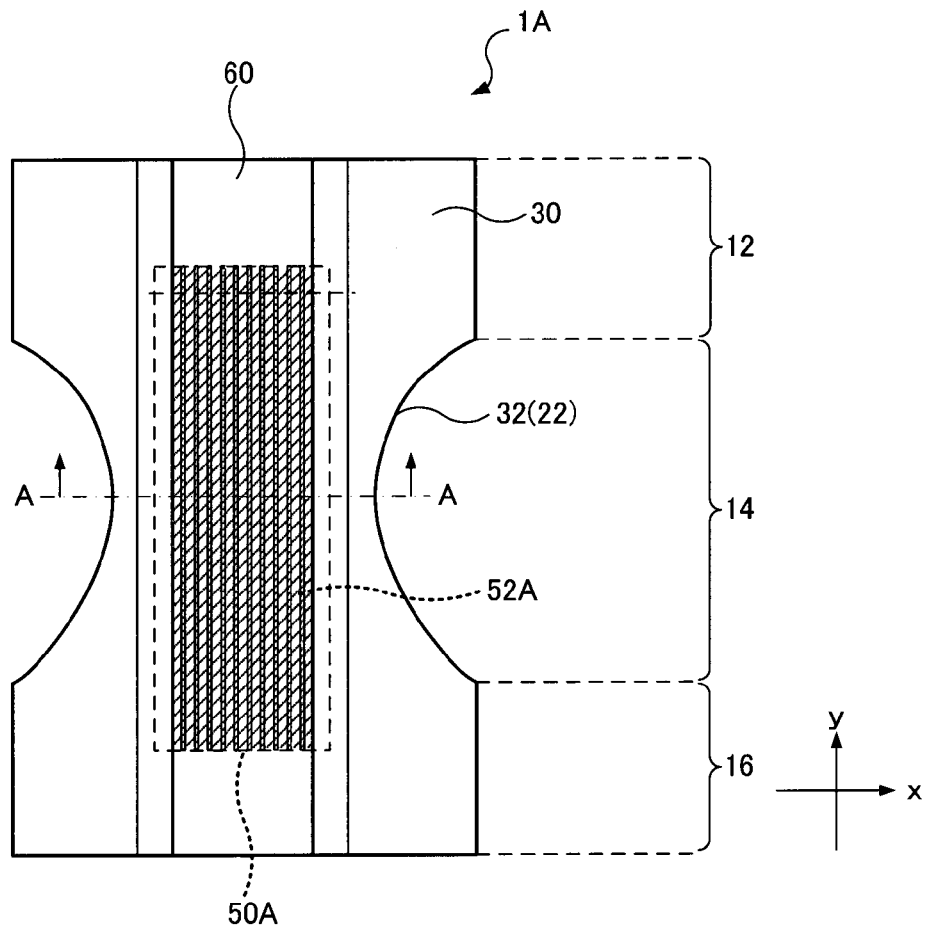
FIG. 1 is a drawing explaining an absorbent article of a first embodiment of the present invention.
Figure 1:
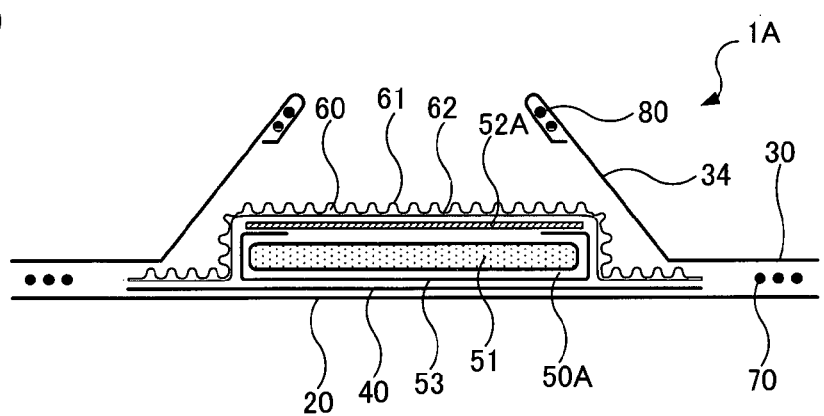

FIG. 1 is a drawing explaining the absorbent article of the first embodiment of the present invention. FIG. 1(a) is an overhead view of the absorbent article of the first embodiment of the present invention, while FIG. 1(b) is a schematic drawing of a cross-section A-A of the absorbent article in the first embodiment of the present invention. An absorbent article 1A in the first embodiment can be divided into a front torso-surrounding area 12 that covers the lower abdomen of a wearer when the diaper is worn by a wearer, a crotch area 14 that covers the crotch of a wearer when the diaper is worn by a wearer, and a rear torso-surrounding area 16 that covers the buttocks of a wearer when the diaper is worn by a wearer. In FIG. 1(a), the lengthwise direction of the absorbent article 1A is that of the y axis, while the widthwise direction perpendicular to the lengthwise direction is that of the x axis. In addition, the diaper laid flat as shown in FIG. 1(a) is substantially planar and may be considered to lie in the xy plane.

The absorbent article 1A is provided with a chassis 20, which has curved notched portions 22 on two sides in the widthwise direction of a rectangle, flaps 30, may be provided in areas on both sides in the widthwise direction of the chassis 20 and which have a notched portion 32 of which the edge is of the same shape as the notched portion 22 of the chassis 20, a back sheet 40 provided in an area in the center of the chassis 20 in the widthwise direction, an absorbent 50A provided on the back sheet 40, and a top sheet 60 provided on the absorbent 50A. Openings are formed around the legs of a wearer by the two notched portions 22 and 32 of the chassis 20 and the flaps 30. The area of the chassis 20 and the flaps 30 in the absorbent article 1A between the two notched portions 22 and 32 is the crotch area 14. One of the adjacent areas to a front side in the lengthwise direction of the crotch area 14 is the front torso-surrounding area 12, and the other area is the rear torso-surrounding area 16. A stretchable material 70 that extends in the lengthwise direction of the absorbent article 1A may be provided between the vicinity of the edges in the widthwise direction of the chassis 20 and the vicinity of the edges in the widthwise direction of the flaps 30. In addition, a stretchable material 80 that extends in the lengthwise direction of the absorbent article 1A may also provided in the vicinity of the edges of the flaps 30 in the center of the absorbent article 1A.

The chassis 20 forms the exterior of the body of the absorbent article 1A. A porous non-woven fabric or plastic film is used for the chassis 20 to prevent a lack of breathability when wearing. The flaps 30 cover the areas around the legs of a wearer as well as both sides of the upper abdomen and buttocks. A hydrophobic non-woven fabric is used for the flaps 30. The stretchable material 70 provided between the chassis 20 and the flaps 30 ensures a proper fit of the absorbent article 1A around the legs. In addition, leakage preventive walls 34 are formed by raising up the center of the flaps 30 due to contractile force of the stretchable material 80 provided in the vicinity of the edges of the flaps 30 in the center of the absorbent article 1A and prevent urine or soft stool from leaking from the location in the widthwise direction of the crotch region 14 of the absorbent article 1A. Natural rubbers, synthetic rubbers or elastic fibers such as spandex may be used for the stretchable materials 70 and 80.

The back sheet 40 is a liquid-impermeable sheet that does not allow the passage of urine, and is provided to prevent discharged urine from leaking to the outside. For example, a waterproofed non-woven fabric, a plastic film composed of polyethylene, or a composite material of a non-woven fabric and a plastic film, may be used for the back sheet 40.

The absorbent 50A absorbs and retains urine of a wearer. For example, the absorbent 50A is mainly composed of an absorbent member 51, such as crushed pulp, highly absorbent polymer or hydrophilic sheet, and upper and lower covering sheets 52A and 53, such as tissue paper enclosing an absorbent member or non-woven fabric subjected to hydrophilic treatment. The upper covering sheet 52A covers the top sheet side (skin-facing side) surface of the absorbent member 51, and the lower covering sheet covers the other surface (garment-facing side surface) of the absorbent member 51. The upper covering sheet 52A is colored to a color other than white, such as a chromatic color such as blue or green or an achromatic color such as gray. The covering sheets 52A and 53 may be adhered to the absorbent member 51 with an adhesive such as a hot melt adhesive. The adhesive may be coated onto the absorbent member 51 or the covering sheets 52A and 53 by spiral coating, curtain coating and the like.

The top sheet 60 is a liquid-permeable sheet that rapidly absorbs urine of a wearer and transfers it to the absorbent 50A. Since the top sheet 60 contacts the skin of the wearer, it is desirable required to feel comfortable against the skin and be safe for the skin. The surface of the top sheet 60 that contacts the skin of the wearer is hereinafter referred to as the skin contact surface, while the surface opposite from the skin contact surface is hereinafter referred to as the non-skin contact surface. In addition, it is also desirable that the top sheet 60 does not allow urine absorbed by the absorbent to return. The top sheet 60 is preferably adhered to the absorbent 50A using an adhesive such as a hot melt adhesive to allow urine of the wearer to be rapidly absorbed and transferred to the absorbent 50A. The adhesive is preferably coated onto the top sheet 60 or the upper covering sheet 52A by line coating in order to inhibit reduction of liquid permeability due to the adhesive. The colored upper covering sheet 52A provided on the non-skin contact surface of the top sheet 60 is visible through the top sheet 60. The top sheet 60 is preferably a non-woven fabric having a plurality of protrusions 61 protruding in the thickness direction and extending in the lengthwise direction, and a plurality of indentations 62 indented in the thickness direction and extending in the lengthwise direction. The distance between apices of adjacent protrusions 61 is, for example, 4 mm. The plurality of protrusions 61 and the plurality of indentations 62 are alternately arranged in the widthwise direction. The non-woven fabric used for the top sheet 60 preferably contains fibers for which the intersections thereof are adhered by hot melting. Such fibers may be, for example, fibers composed of a thermoplastic polymer material, such as a polyolefin such as polyethylene or polypropylene, a polyester such as polyethylene terephthalate, or a polyamide. In addition, core-sheath types or side-by-side types of composite fibers composed of a combination of a plurality of thermoplastic polymers may also be used for these fibers.

The color of the top sheet 60 is preferably white. Furthermore, the "white color" described in this description also includes white color tinted with other colors in addition to pure white color.

Figure 2:
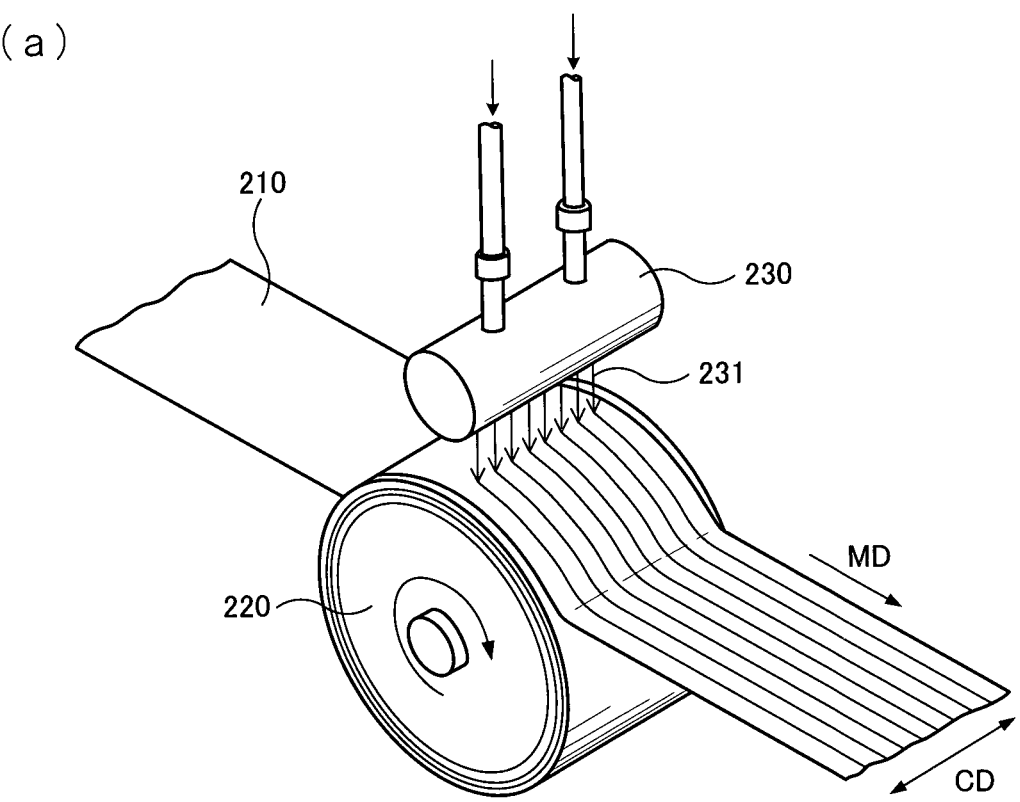
FIG. 2 is a drawing explaining a method and equipment for forming a plurality of protrusions protruding in the thickness direction and a plurality of indentations indented in the thickness direction in a top sheet.
Figure 2:
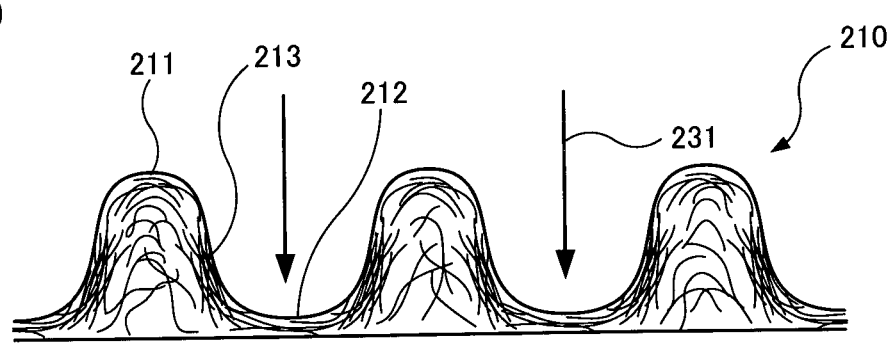

Next, an explanation is provided of an example of a method for forming the plurality of protrusions 61 protruding in the thickness direction and the plurality of indentations 62 indented in the thickness direction in the top sheet with reference to FIG. 2. FIG. 2(a) is a drawing for explaining a process for forming protrusions and indentations in a web formed to produce a non-woven fabric, while FIG. 2(b) is a drawing showing a cross-section in a widthwise direction (CD) of a web in which protrusions and indentations have been formed. A web 210, formed by web forming means such as a carding machine, is transported to a suction drum 220. A heated fluid 231 is discharged onto the web 210 over a portion of the web 210 from nozzles of a discharge unit 230 to form protrusions 211 and indentations 212 in the web 210. Fibers that have been pushed apart in the widthwise direction (CD) perpendicular to the machine direction (MD), which is the direction of travel of the web 210, gather in the protrusions 211, and particularly on the side portions 213 of the protrusions 211. Thus, since fibers of an area equivalent to the indentations 212 are deposited in the protrusions 211, the basic weight of the protrusions 211, and particularly the side portions 213 of the protrusions 211, increases. In addition, since fibers are dispersed in the widthwise direction (CD) by the heated fluid 231, the basic weight of the indentations 212 is low.

The heated fluid 231 that has been discharged from the discharge unit 230 may be a gas such as air or water vapor or a liquid such as water. In addition, it may also be an aerosol containing fine particles of a solid or liquid in a gas.

Figure 3:
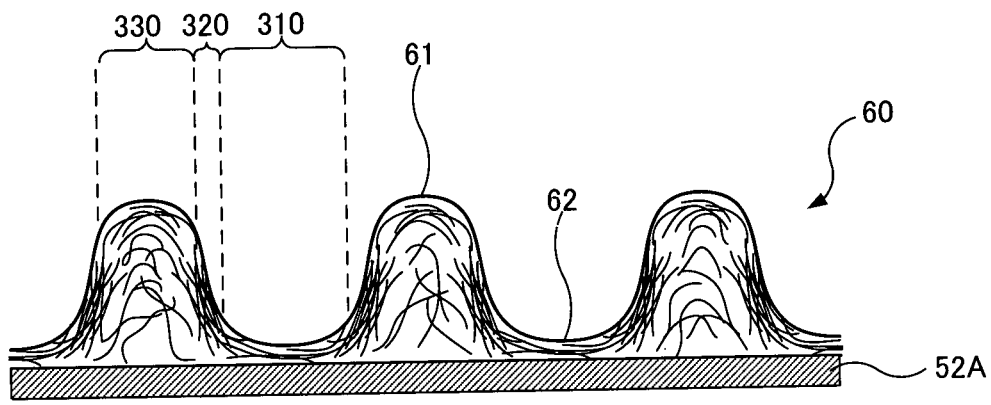
FIG. 3 is a drawing explaining an upper covering sheet visible through a top sheet.
Figure 3:
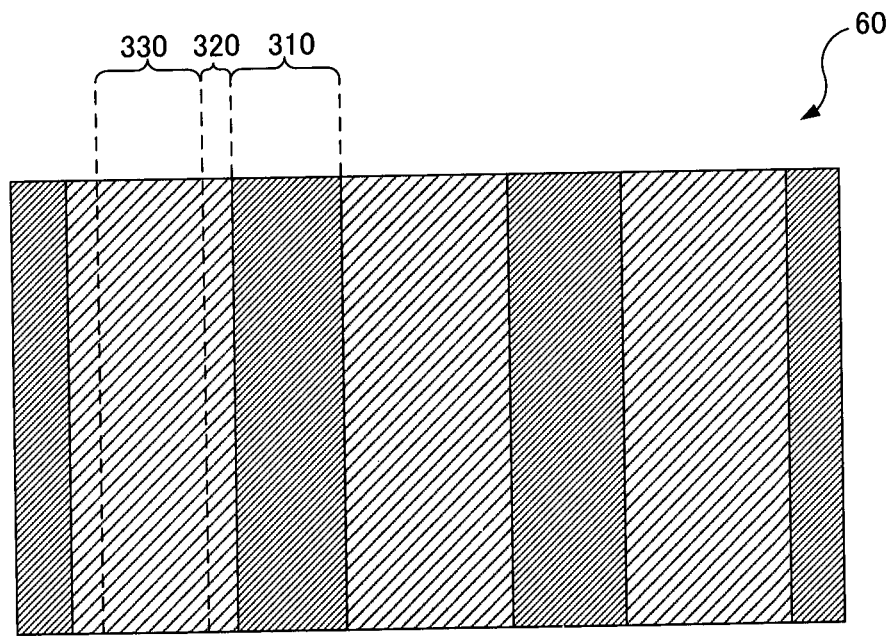

Next, an explanation is provided of the upper covering sheet 52A visible through the top sheet 60 with reference to FIG. 3. The upper covering sheet 52A is also referred to herein as "colored upper covering sheet 52A". FIG. 3(a) is a cross-sectional view of the top sheet 60 and the upper covering sheet 52A provided on the non-skin contact surface of the top sheet 60, and FIG. 3(b) is a drawing explaining the upper covering sheet 52A visible through the top sheet 60. In an area 310 at the bottom of the indentations 62 (corresponding to indentations 212 described with respect to FIG. 2) of the top sheet 60, since the thickness of the top sheet 60 is less and the basic weight is lower, the upper covering sheet 52A can be easily seen through the top sheet 60. Thus, the color of the upper covering sheet 52A appears darker in the area 310 at the bottom of the indentations 62 of the top sheet 60 than that in a side edge region 320 on the side portions of the protrusions 61 (corresponding to protrusions 211 described with respect to FIG. 2) of the top sheet 60 and that in an area 330 of the apices of the protrusions 61 of the top sheet 60. In the side edge region 320 on the side portions of the protrusions 61 of the top sheet 60, although the thickness of the top sheet 60 is not that thick, since the basic weight is high, the upper covering sheet 52A may not be seen easily through the top sheet 60. Thus, the color of the upper covering sheet 52A either appears lighter or appears white in the side edge region 320 on the side portions of the protrusions 61 of the top sheet 60. In the area 330 of the apices of the protrusions 61 of the top sheet 60, since the top sheet 60 is thick and has high basic weight, the upper covering sheet 52A cannot be easily seen through the top sheet 60. Thus, the color of the upper covering sheet 52A appears lighter or appears white in the area 330 of the apices of the protrusions 62 of the top sheet 60.

The color difference between the Lab value of the color of the upper covering sheet 52A visible through the protrusions 61 of the top sheet 60 and the Lab value of the color of the upper covering sheet 52A visible through the indentations 62 of the top sheet 60 is 2.8 or more. If the color difference between the Lab value of the color of the upper covering sheet 52A visible through the protrusions 61 of the top sheet 60 and the Lab value of the color of the upper covering sheet 52A visible through the indentations 62 of the top sheet 60 is less than 2.8, the distinction of the color of the upper covering sheet 52A visible through the protrusions 61 of the top sheet 60 from the color of the upper covering sheet 52A visible through the indentations 62 of the top sheet 60 may be unrecognizable with the naked eye. In addition, the difference between the manner in which the upper covering sheet 52A appears through the protrusions 61 of the top sheet 60 and the manner in which the upper covering sheet 52A appears through the indentations 62 of the top sheet 60 is small, and visibility of the protrusions 61 and the indentations 62 of the top sheet 60 may not improve as desired due to a low difference in color.

The percentage of surface area of the protrusions 61 in the top sheet 60 is preferably 50% to 75% and more preferably 65% to 75%. In addition the percentage of surface area of the indentations 62 is preferably 25% to 50% and more preferably 25% to 35%. In the case the percentages of the surface areas of the protrusions 61 and the indentations 62 are within these ranges, surface irregularities in the top sheet 60 are particularly emphasized by different visibility of the upper covering sheet 52A through different regions, e.g., the protrusions 61 and the indentations 62, of the top sheet 60.

The absorbent article 1A of the first embodiment of the present invention as described above demonstrates the actions and effects indicated below.

(1) An absorbent article 1A provided with a liquid-permeable top sheet 60 composed of a white non-woven fabric, a liquid-impermeable back sheet 40 provided at a location opposing the top sheet, and an absorbent 50A provided between the top sheet 60 and the back sheet 40, wherein an upper covering sheet 52A is further provided on the non-skin contact surface of the top sheet 60 that is visible through the top sheet and is colored to a color other than white, the top sheet 60 has a plurality of protrusions 61 protruding in the thickness direction and a plurality of indentations 62 indented in the thickness direction, the plurality of protrusions 61 and the plurality of indentations 62 extend in the lengthwise direction and are alternately arranged in the widthwise direction, the basic weight of the protrusions 61 is greater than the basic weight of the indentations 62, and the color difference between the color of the upper covering sheet 52A visible through the protrusions 61 of the top sheet 60 and the color of the upper covering sheet 52A visible through the indentations 62 of the top sheet 60 is 2.8 or more. As a result, the surface irregularities of the protrusions 61 and the indentations 62 on the skin contact surface of the top sheet 60 of the absorbent article 1A can be accurately emphasized. The existence of an enhanced function of the surface of the top sheet 60 of the absorbent article 1A can be immediately and readily conveyed to a user. In addition, since a striped pattern (e.g., of the protrusions 61 and the indentations 62) can be imparted to the absorbent article 1A, the absorbent article 1A can be made to have a superior design. In addition, following use of the absorbent article 1A, the protrusions 61 of the top sheet 60 appear whiter and more three-dimensional than the indentations 62 through which visible from the upper covering sheet 52A is visible. Consequently, the portion of the protrusions 61 in direct contact with the skin of a wearer can be recognized by a user to be whiter and less soiled, thereby giving an impression of a high sense of cleanliness to the user.

(2) The basic weight of the side edge region 320 on the side portions of the protrusions 61 is greater than the basic weight of other areas, e.g., 330, of the protrusions 61. As a result, the difference between the color of the upper covering sheet 52A visible through the protrusions 61 of the top sheet 60 and the color of the upper covering sheet 52A visible through the indentations 62 of the top sheet 60 in the vicinity of the boundary between the protrusions 61 and the indentations 62 becomes greater.

(3) The absorbent 50A is provided on the non-skin contact surface of the top sheet 60, and absorbent member 51 of the absorbent 50A is enclosed by one or more covering sheets 52A and 53, and at least one of the covering sheets 52A and 53 is colored to a color other than white. As a result, the surface irregularities of the protrusions 61 and the indentations 62 irregularities 61 and 62 are emphasized on the skin contact surface of the top sheet 60 only in the area where the absorbent 50A is present, enabling a user to easily determine the area where the absorbent 50A is present. In addition, as a result of only emphasizing the surface irregularities of the protrusions 61 and the indentations 62 on the skin contact surface of the top sheet 60 in the area where the absorbent 50A is present, the absorbent article 1 is able to give the impression of having an extremely high absorbency to a user. At least a portion of one or more of the covering sheets 52A and 53 may be colored to a color other than white the surface, if irregularities 61 and 62 are emphasized on the skin contact surface of the top sheet 60 only in the area where the absorbent 50A is present.

Second Embodiment

The following provides an explanation of an absorbent article of a second embodiment of the present invention with reference to the drawings. The absorbent article of the second embodiment is also a disposable diaper, however, as specified in paragraph 0008 above, and as will be readily appreciated by those skilled in the art, the absorbent article need not be limited to a disposable diaper nor to an absorbent article of the form described. The top sheet of nonwoven fabric and the colored element of the second embodiment may be taken in isolation of the disclosed diaper and applied to alternative absorbent articles that also feature a backsheet and an absorbent.

Figure 4:
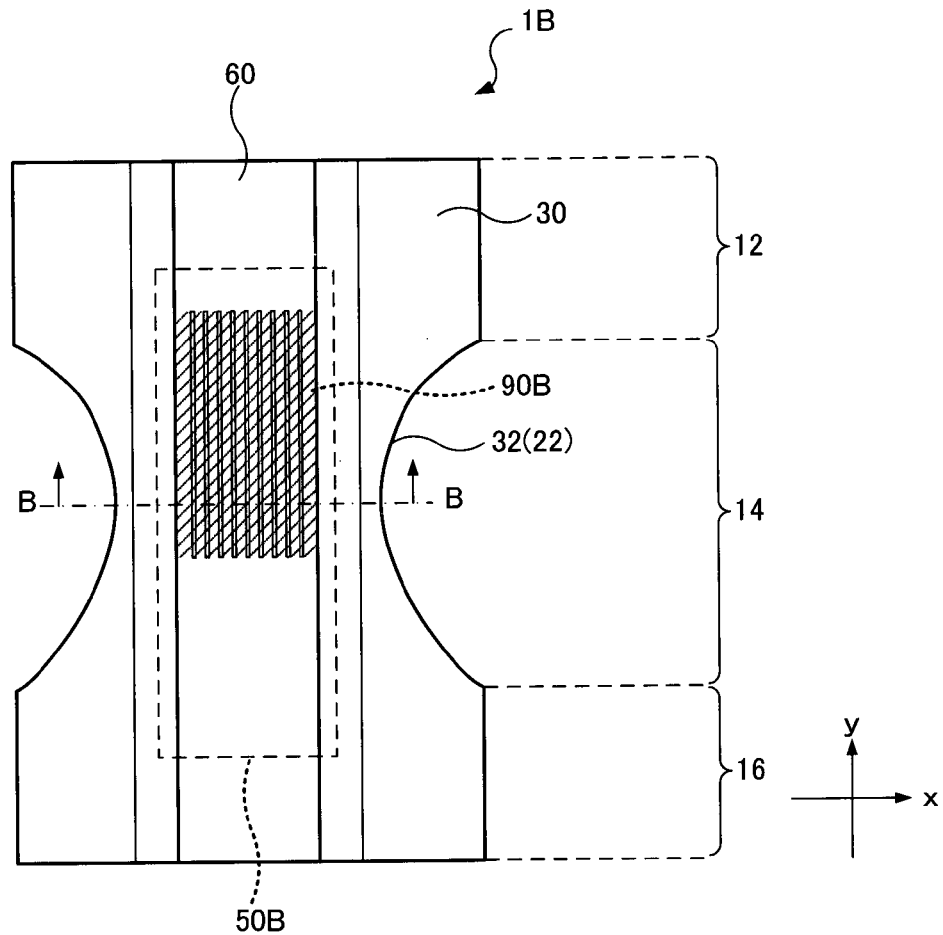
FIG. 4 is a drawing explaining an absorbent article of a second embodiment of the present invention.
Figure 4:
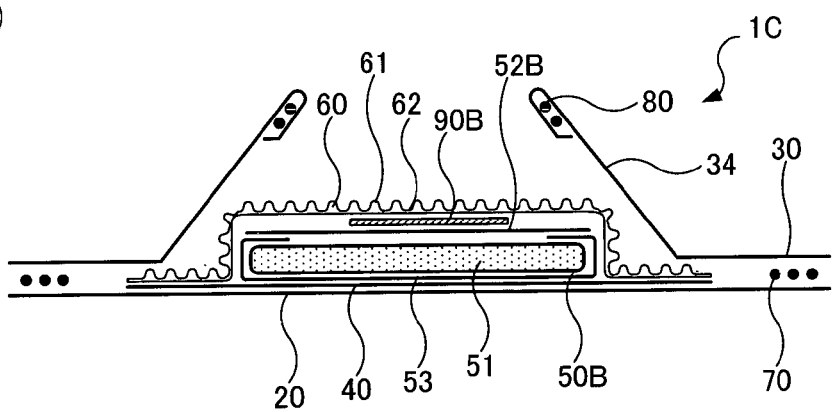

FIG. 4 is a drawing explaining the absorbent article of the second embodiment of the present invention. FIG. 4(a) is an overhead view of the absorbent article in the second embodiment of the present invention, while FIG. 4(b) is a schematic diagram of a cross-section B-B of the absorbent article in the second embodiment of the present invention. In addition, in FIG. 4(a), the lengthwise direction of an absorbent article 1B is the direction of the y axis, the widthwise direction perpendicular to the lengthwise direction is the direction of the x axis, and with the diaper laid flat as shown in FIG. 4(a) it is substantially planar and may be considered to lie in the xy plane. The same reference symbols are used to indicate those constituents of the absorbent article 1B in the second embodiment that are similar to constituents of the absorbent article 1A in the first embodiment, and an explanation is mainly provided for those portions that differ from the absorbent article 1A in the first embodiment. The absorbent article 1B of the second embodiment has a second sheet 90B between the top sheet 60 and an absorbent 50B.

The absorbent article 1B is provided with the chassis 20, the flaps 30, the back sheet 40, the absorbent 50B provided on the back sheet 40, the second sheet 90B provided on the absorbent 50B, and the top sheet 60 provided on the second sheet 90B.

An upper covering sheet 52B, which covers the top sheet side surface of the absorbent member 51 in the absorbent 50B, differs from the upper covering sheet 52A of the absorbent article 1A of the first embodiment in that it is not colored.

The second sheet 90B is used to disperse urine of a wearer released onto the top sheet 60 and improve cushioning of the skin contact surface of the absorbent article 1B. A hydrophilic, liquid-permeable material such as a woven fabric, non-woven fabric, porous plastic or fluff pulp can be used for the second sheet 90B. The second sheet 90B is colored to a color other than white such as a chromatic color such as blue or green or an achromatic color such as gray.

The second sheet 90B is provided to overlap at least a portion of the absorbent 50B. The second sheet 90B preferably has a smaller area than the absorbent so that it covers a region only of the absorbent. For example, as shown in FIG. 4(a), the second sheet 90B is provided at a location corresponding to an outlet of urine of a wearer (urination point) and its surrounding area (absorption zone), or in other words, in an area of the front torso-surrounding area 12 side of the absorbent 50B. Thus, since the area of the absorption zone differs between the absorbent article 1B for use by men and the absorbent article 1B for use by women, the areas where the second sheet 90B is provided may also differ between the absorbent article 1B for use by men and the absorbent article 1B for use by women. Namely, the area where the second sheet 90B is provided in the absorbent article 1B for use by men is closer to the front torso-surrounding area 12 side than the area where the second sheet 90B is provided in the absorbent article 1B for use by women. In addition, since the surface irregularities of the protrusions 61 and the indentations 62 of the skin contact surface of the top sheet 60 are emphasized only in the area of the absorption zone of the top sheet 60, a user can easily recognize the absorption zone. The top sheet 60 of the area where the second sheet 90B is provided has greater bulk than the area where the second sheet 90B is not provided.

In order to allow urine of a wearer to be rapidly absorbed and transferred to the absorbent 50B, the second sheet 90B may be adhered to the top sheet 60 and the absorbent 50B using an adhesive such as a hot melt adhesive. In addition, as a result of the basic weight being greater than that of the top sheet 60 and using a high density material for the second sheet 90B, liquid can be made to be favorably transferred from the top sheet 60 to the second sheet 90B.

The second sheet 90B may be adhered to the absorbent 50B using an adhesive such as a hot melt adhesive. The adhesive may be coated onto the second sheet 90B or the absorbent 50B by spiral coating, curtain coating and the like.

Urine released onto the top sheet 60 passes through the second sheet 90B and is absorbed by the absorbent 50B. Thus, since urine does not remain in the top sheet 60 or the second sheet 90B, there is little change in the color of the top sheet 60 and the second sheet 90B caused by the color of the urine. Consequently, even after urine has been received, the surface irregularities of the protrusions 61 and the indentations 62 on the skin contact surface of the top sheet 60 are emphasized in the same manner as before the urine discharge. As a result, even after urine has been received, an impression that the skin contact surface of the absorbent article 1B is dry can be given to a user.

The color difference between the color of the second sheet 90B visible through the protrusions 61 of the top sheet 60 and the color of the second sheet 90B visible through the indentations 62 of the top sheet 60 is again 2.8 or more. If the color difference between the color of the second sheet 90B visible through the protrusions 61 of the top sheet 60 and the color of the second sheet 90B visible through the indentations 62 of the top sheet 60 is less than 2.8, the distinction of the color of the second sheet 90B visible through the protrusions 61 of the top sheet 60 from the color of the second sheet 90B visible through the indentations 62 of the top sheet 60 may be unrecognizable with the naked eye. In addition, if the color difference is less than 2.8, the difference between the manner in which the second sheet 90B appears through the protrusions 61 of the top sheet 60 and the manner in which the second sheet 90B appears through the indentations 62 of the top sheet 60 is small, and visibility of the protrusions 61 and the indentations 62 of the top sheet 60 may not improve as desired due to a low difference in color.

The absorbent article 1B of the second embodiment of the present invention as described above demonstrates the actions and effects indicated below.

(1) An absorbent article 1B provided with a liquid-permeable top sheet 60 composed of a white non-woven fabric, a liquid-impermeable back sheet 40 provided at a location opposing the top sheet 60, and an absorbent 50B provided between the top sheet 60 and the back sheet 40, wherein a second sheet 90B is further provided on the non-skin contact surface of the top sheet 60 that is visible through the top sheet 60 and is colored to a color other than white, the top sheet 60 has a plurality of protrusions 61 protruding in the thickness direction and a plurality of indentations 62 indented in the thickness direction, the plurality of protrusions 61 and the plurality of indentations 62 extend in the lengthwise direction and are alternately arranged in the widthwise direction, the basic weight of the protrusions 61 is greater than the basic weight of the indentations 62, and the color difference between the color of the second sheet 90B visible through the protrusions 61 of the top sheet 60 and the color of the second sheet 90B visible through the indentations 62 of the top sheet 60 is 2.8 or more. As a result, the surface irregularities of the protrusions 61 and the indentations 62 on the skin contact surface of the top sheet 60 in the area where the second sheet 90B is provided can be accurately emphasized.

(2) The basic weight of the area on the side portions of the protrusions 61 is greater than the basic weight of other areas of the protrusions 61. As a result, the difference between the color of the second sheet 90B visible through the protrusions 61 of the top sheet 60 and the color of the second sheet 90B visible through the indentations 62 of the top sheet 60 in the vicinity of the boundary between the protrusions 61 and the indentations 62 becomes greater.

(3) The second sheet 90B is provided to overlap a portion only of the absorbent 50B. As a result, by providing the second sheet 90B in an area such as an absorption zone of the absorbent article 1B, a user can easily recognize such an area, i.e., the absorbent zone.

(4) The area in the planar direction where the second sheet 90B is provided differs between a diaper for use by men and a diaper for use by women. As a result, an absorption zone of a disposable diaper can be easily recognized, so that a user can determine whether the diaper is for use by men or by women. More specifically, the location where the second sheet 90B is provided is preferably near a urination point in order to inhibit liquid transfer and return of urine from the absorbent 50B. The location where the second sheet 90B of a diaper for use by men is provided is preferably roughly 15 to 30 mm towards the front torso-surrounding area 12 in comparison with location where the second sheet 90B is provided in a diaper for use by women. As a result, the colored second sheet 90B is suitably present in the vicinity of the urination point of a wearer, and as a result of it being easy to recognize that there are surface irregularities in the vicinity of the urination point of the diaper, a user can effectively recognize that the absorbency of the diaper is enhanced.

Third Embodiment

The following provides an explanation of an absorbent article of a third embodiment of the present invention with reference to the drawings. The absorbent article of the third embodiment of the present invention is also a disposable diaper, however, as specified in paragraph 0008 above, and as will be readily appreciated by those skilled in the art, the absorbent article need not be limited to a disposable diaper nor to an absorbent article of the form described. The top sheet of nonwoven fabric and the colored element of the third embodiment may be taken in isolation of the disclosed diaper and applied to alternative absorbent articles that also feature a backsheet and an absorbent.

Figure 5:
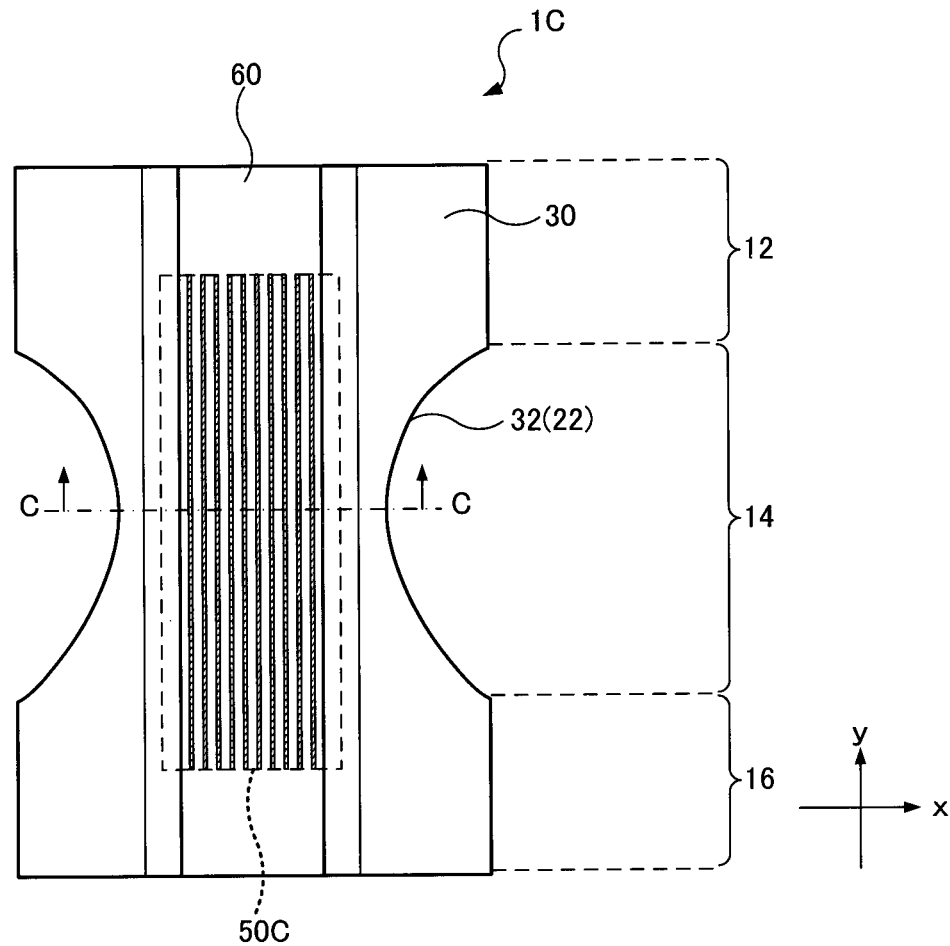
FIG. 5 is a drawing explaining an absorbent article of a third embodiment of the present invention.
Figure 5:
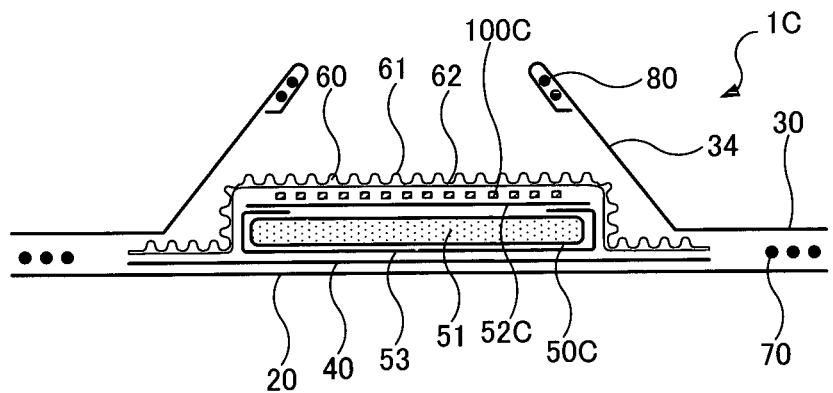

FIG. 5 is a drawing for explaining the absorbent article of the third embodiment of the present invention. FIG. 5(a) is an overhead view of the absorbent article in the third embodiment of the present invention, while FIG. 5(b) is a schematic diagram of a cross-section C-C of the absorbent article in the third embodiment of the present invention. In addition, in FIG. 5(a), the lengthwise direction of an absorbent article 1C is the direction of the y axis, the widthwise direction perpendicular to the lengthwise direction is the direction of the x axis, and with the diaper laid flat as shown in FIG. 5(a) it is substantially planar and may be considered to lie in the xy plane. The same reference symbols are used to indicate those constituents of the absorbent article 1C in the third embodiment that are similar to constituents of the absorbent article 1A in the first embodiment, and an explanation is mainly provided for those portions that differ from the absorbent article 1A in the first embodiment. In the absorbent article 1C of the third embodiment, an adhesive for adhering the top sheet 60 to the absorbent 50C is colored to a color other than white, such as a chromatic color such as blue or green or an achromatic color such as gray.

The absorbent article 1C is provided with the chassis 20, the flaps 30, the back sheet 40, an absorbent 50C provided on the back sheet 40, and the top sheet 60 provided on the absorbent 50C.

A upper covering sheet 52C that covers the top surface sheet side of the absorbent member 51 differs from the upper covering sheet 52A of the absorbent article 1A of the first embodiment in that it is not colored.

The top sheet 60 is adhered to the absorbent 50C using an adhesive 100C such as a hot melt adhesive. The adhesive 100C is coated at a location on the non-skin contact surface of the top sheet 60 opposing the indentations 62 or at a location on the top sheet side of the absorbent 50C opposing the indentations 62 of the top sheet 60. Namely, the adhesive 100C is coated in the form of bands (strips) extending in the lengthwise direction coinciding with the indentations 62 of the top sheet 60 extending in the lengthwise direction. The width of the bands where the adhesive 100C is provided is preferably less than the width of the indentations 62 in the widthwise direction. For example, in the case the width in the widthwise direction of the indentations 62 is 1 mm, then the adhesive 100C is coated in the lengthwise direction on the non-skin contact surface of the top sheet 60 or the top sheet side surface of the absorbent 50C in bands having widths of 0.8 mm. Here, the width of an indentation 62 is the dimension in the widthwise from (i) an intermediate location between the apex of an adjacent protrusion 61 and a lowermost portion of the indentation 62 to (ii) another intermediate location between the apex of another adjacent protrusion 61 and the lowermost portion of the indentation 62. As a result, since the area opposing the protrusions 61 of the non-skin contact surface of the top sheet 60 are not colored, while the area opposing the indentations 62 of the non-skin contact surface of the top sheet 60 is colored, the difference in the manner in which color appears between the protrusions 61 and the indentations 62 of the top sheet 60 increases.

In this case, the color difference between the color of an upper covering sheet 52C visible through the protrusions 61 of the top sheet 60 and the color of the adhesive 100C visible through the indentations 62 of the top sheet 60 is 2.8 or more. If the color difference between the color of the upper covering sheet 52C visible through the protrusions 61 of the top sheet 60 and the color of the adhesive 100C visible through the indentations 62 of the top sheet 60 is less than 2.8, it may not be possible to distinguish between the color of an upper covering sheet 52C visible through the protrusions 61 of the top sheet 60 and the color of the adhesive 100C visible through the indentations 62 of the top sheet 60 by observing with the naked eye. In addition, if the color difference between the color of an upper covering sheet 52C visible through the protrusions 61 of the top sheet 60 and the color of the adhesive 100C visible through the indentations 62 of the top sheet 60 is less than 2.8, the difference between the manner in which the upper covering sheet 52C appears through the protrusions 61 of the top sheet 60 and the manner in which the adhesive 100C appears through the indentations 62 of the top sheet 60 becomes small, and visibility of the protrusions 61 and the indentations 62 of the top sheet 60 may not improve as desired due to a low difference in color.

In addition, even if the area where the adhesive 100C is coated is shifted slightly in the widthwise direction from the area corresponding to the indentations 62 of the top sheet 60, since a portion that is not colored always appears in the area opposing the protrusions 61 of the non-skin contact surface of the top sheet 60 and a portion that is colored always appears in the area opposing the indentations 62 of the non-skin contact surface of the top sheet 60, the difference in the manner in which color appears between the protrusions 61 and the indentations 62 of the top sheet 60 is always large. In this case, the color difference between the color of the adhesive 100C visible through the protrusions 61 of the top sheet 60 and the color of the adhesive 100C visible through the indentations 62 of the top sheet 60 is 2.8 or more. As a result, the surface irregularities of the protrusions 61 and the indentations 62 on the skin contact surface of the top sheet 60 of the absorbent article 1C can be accurately emphasized.

The absorbent article 1C of the third embodiment of the present invention as described above demonstrates the actions and effects indicated below.

An absorbent article 1C provided with a liquid-permeable top sheet 60 composed of a white non-woven fabric, a liquid-impermeable back sheet 40 provided at a location opposing the top sheet 60, and an absorbent 50C provided between the top sheet 60 and the back sheet 40, wherein an adhesive 100C is further provided between the top sheet 60 and the absorbent 50C that is visible through the top sheet 60 and is colored to a color other than white, the top sheet 60 has a plurality of protrusions 61 protruding in the thickness direction and a plurality of indentations 62 indented in the thickness direction, the plurality of protrusions 61 and the plurality of indentations 62 extend in the lengthwise direction and are alternately arranged in the widthwise direction, the basic weight of the protrusions 61 is greater than the basic weight of the indentations 62, the color difference between the color of the adhesive 100C visible through the protrusions 61 of the top sheet 60 and the color of the adhesive 100C visible through the indentations 62 of the top sheet 60 is 2.8 or more, the adhesive 100C is provided at a location of the non-skin contact surface of the top sheet 60 to coincide with the indentations 62 of the top sheet 60, and the width of the adhesive 100C in each of the areas where the adhesive 100C is provided is less than the width in the widthwise direction of the indentations 62, namely less than the width thereof. As a result, the surface irregularities of the protrusions 61 and the indentations 62 of the skin contact surface of the top sheet 60 can be accurately emphasized. In addition, since the region of the non-skin contact surface of the top sheet 60 opposing the protrusions 61 is not colored that much, while the area of the non-skin contact surface of the top sheet 60 opposing the indentations 62 is colored, the difference in the manner in which color appears between the protrusions 61 and the indentations 62 of the top sheet 60 becomes large, thereby making it possible to further emphasize the surface irregularities of the protrusions 61 and the indentations 62 of the skin contact surface.

Examples

Color difference between the color of a colored portion visible through protrusions of a top sheet and the color of a colored portion visible through indentations of a top sheet was measured in the examples.

(Samples)

Example 1 was a disposable diaper according to the First Embodiment in which a covering sheet was colored green, and Example 2 was a disposable diaper according to the Second Embodiment in which a second sheet was colored blue. Both of these examples were samples in which surface irregularities of a top sheet were confirmed to be conspicuously visible in comparison with comparative examples. Absorbent articles that did not have a colored portion (Comparative Example 1: Moony Size L, Unicharm Corp.) were also measured for color difference.

The basic weight of the top sheet of Example 1 was about 30 g/m$^2$, the basic weight of the top sheet of Example 2 was about 25 g/m$^2$, and the basic weight of the top sheet of Comparative Example 1 was about 30 g/m$^2$.

The thickness of the protrusions of the top sheet of Example 1 was 1.3 to 1.5 mm and the thickness of the indentations was 0.4 to 0.6 mm, the thickness of the protrusions of the top sheet of Example 2 was 0.7 to 0.9 mm and the thickness of the indentations was 0.3 to 0.5 mm, and the thickness of the protrusions of the top sheet of Comparative Example 1 was 1.3 to 1.5 mm and the thickness of the indentations was 0.4 to 0.6 mm.

The thicknesses of the protrusions and indentations were measured in the manner described below. Here, the thickness of the protrusions refers to the thickness at the apices of the protrusions, while the thickness of the indentations refers to the thickness of the deepest portion of the indentations.

(1) A piece of fibrous non-woven fabric for measurement of thickness was cut parallel in the widthwise direction (CD) using a cutter knife (standard replacement blade for HA-100B and HA-NB manufactured by Kokuyo Co., Ltd.) to prepare a cross-sections for observation lying in parallel with the widthwise direction (CD) in the fibrous non-woven fabric. Subsequently, the surface of the fibrous non-woven fabric was placed on a horizontal surface H and micrographs of the cross-section for observation were obtained at a magnification of 25× using the Model VHX-100 Keyence Digital Microscope.

(2) The cross-sectional micrographs were processed with image processing software in the form of USB Digital Image Analysis Software manufactured by Scalar Corp. followed by binarization of the resulting images. At that time, the threshold value was set to 50. "Hole-filling" was selected for the arithmetic processing method of binary image morphology analysis of the binarized images, followed by processing by selecting "white" for the target color. Moreover, "hole-filling" was again selected for the arithmetic processing method of binary image morphology analysis, followed by processing by selecting "black" for the target color. Staple fibers that protruded to the outside from groups of staple fibers in the form of white islands were removed from the images on which processing was completed to obtain corrected CD cross-sectional micrographs free of unraveled fibers.

(3) In the corrected micrographs, the distance from the apex of a protrusion to the horizontal surface H on which the samples were placed was defined as the thickness of the protrusions.

(4) The distance from the bottom of an indentation perpendicular to the horizontal surface H to the horizontal surface on which the samples were placed was defined as the thickness of the indentations.

(Color Difference Measurement Method)

(1) Top sheets of Examples 1 and 2 and Comparative Example 1 were photographed under the conditions indicated below.

Camera used for photography: Canon IXY Digital 5.0 Megapixels

Photography environment: Samples were illuminated using the Cool Light CL-570PX manufactured by LPL Corp (lamp: PHOTOLUX57 (57 W×1 lamp), color temperature: approx. 5000 K) which was mounted directly above the sample. The distance between the Cool Light CL-570PX and the sample is 80-100 cm.

Photographing distance: 20 cm (2) Image data obtained by photographing the samples was analyzed using image editing software (Microsoft® Paint Ver. 5.1).

(3) The center in the widthwise direction of protrusions and the center in the widthwise direction of indentations in images of the top sheets were designated according to the following procedure, and RGB values were displayed and measured at the designated locations.

The locations where RGB values were displayed were designated after selecting "Select Color" from the menu in the tool bar, and RGB values were displayed when "Edit Color" was selected from the menu followed by selection of "Generate Color".

RGB values were measured for 10 locations for each of protrusions and indentations, and color difference was calculated using the average value of the 10 RGB values.

(4) The mean value of RGB values of protrusions of the top sheets and the mean value of RGB values of indentations were converted to XYZ values, and then further converted to Lab values to calculate color difference.

The RGB values of protrusions and the RGB values of indentations of the top sheets were respectively converted to XYZ values using the following formulas.

$$X = 0.6069R + 0.1735G + 0.2003B$$

$$Y = 0.2989R + 0.5866G + 0.1144B$$

$$Z = 0.0661G + 1.1157B$$

The XYZ values of the protrusions and the XYZ values of the indentations of the top sheets were respectively converted to Lab values using the following formulas:

$$L = 116(Y/Yn)^{1/3} - 16$$

$$a = 500\{(X/Xn)^{1/3} - (Y/Yn)^{1/3}\}$$

$$b = 200\{(Y/Yn)^{1/3} - (Z/Zn)^{1/3}\}$$

wherein,
$(Y/Yn) > 0.008856$
$(X/Xn) > 0.008856$
$(Z/Zn) > 0.008856$

In addition, in the case there were values for (X/Xn), (Y/Yn) or (Z/Zn) that were equal to or less than 0.008856, (X/Xn), (Y/Yn) and (Z/Zn) were substituted in the manner indicated blow in the formulas used to determine L, a and b:

$$(X/Xn)^{1/3} \rightarrow 7.787(X/Xn) + 16/116$$

$$(Y/Yn)^{1/3} \rightarrow 7.787(Y/Yn) + 16/116$$

$$(Z/Zn)^{1/3} \rightarrow 7.787(Z/Zn) + 16/116$$

wherein,
Xn=98.074
Yn=100.000
Zn=118.232

Color difference $\Delta E_{ab}^*$ between Lab values of protrusions and Lab values of indentations of the top sheets was calculated using the following formula.

$$\Delta E_{ab}^* = \{(\Delta L)^2 + (\Delta a)^2 + (\Delta b)^2\}^{1/2}$$

Here, $\Delta L$ is the difference between the L value of protrusions of a top sheet and the L value of indentations of the top sheet, $\Delta a$ is the difference between the a value of protrusions of a top sheet and the a value of indentations of the top sheet, and $\Delta b$ is the difference between the b value of protrusions of a top sheet and the b value of indentations of the top sheet.

(Measurement Results)

(1) The average values of the RGB values of the protrusions of Example 1 were (R, G, B)=(136, 151, 129), while the average values of the RGB values of the indentations were (R, G, B)=(135, 158, 130).

The color difference $\Delta E$ between the color of the protrusions and the color of the indentations of the top sheet of Example 1 was 10.8. In addition, the color difference between the color of the protrusions and the color of the indentations of the top sheet of Example 1 was able to be clearly recognized by visual observation with the naked eye, and the protrusions of the surface irregularities were further emphasized and visible.

(2) The average values of the RGB values of the protrusions of Example 2 were (R, G, B)=(146, 152, 145), while the average values of the RGB values of the indentations were (R, G, B)=(142, 153, 151).

The color difference $\Delta E$ between the color of the protrusions and the color of the indentations of the top sheet of Example 2 was 2.85. In addition, the color difference between the color of the protrusions and the color of the indentations of the top sheet of Example 2 was able to be recognized by visual observation with the naked eye, and the protrusions of the surface irregularities were able to be visibly recognized to be present.

(3) The average values of the RGB values of the protrusions of Comparative Example 1 were (R, G, B)=(150, 152, 135), while the average values of the RGB values of the indentations were (R, B, B)=(156, 157, 143).

The color difference $\Delta E$ between the color of the protrusions and the color of the indentations of the top sheet of Comparative Example 1 was 2.2. The presence of surface irregularities in the top sheet was unable to be clearly confirmed by visual observation with the naked eye in comparison with Examples 1 and 2.

The absorbent article 1A of a first embodiment of the present invention, the absorbent article 1B of the second embodiment, and the absorbent article 1C of the third embodiment as described above can be modified in the manner described below.

(1) If a colored portion provided in the absorbent articles 1A to 1C is visible through the top sheet 60 on the non-skin contact surface of the top sheet 60 is visible through the top sheet 60, and is colored to a color other than white, then the element which is colored is not limited to the upper covering sheet 52A, the second sheet 90 and the adhesive 100C.

(2) The plurality of protrusions and the plurality of indentations formed in the top sheet are not limited to the protrusions 61 and the indentations 62 extending in the lengthwise direction and alternately arranged in the widthwise direction. For example, the protrusions and indentations may have a circular shape in the xy plane and be formed by embossing the skin contact surface of the top sheet.

(3) Although the upper covering sheet 52A that covers the top cover sheet 60 side of the absorbent 50A was colored in the absorbent article 1A of the first embodiment, a lower covering sheet 53, which covers another surface of the absorbent 50, may also be colored.

Figure 6:
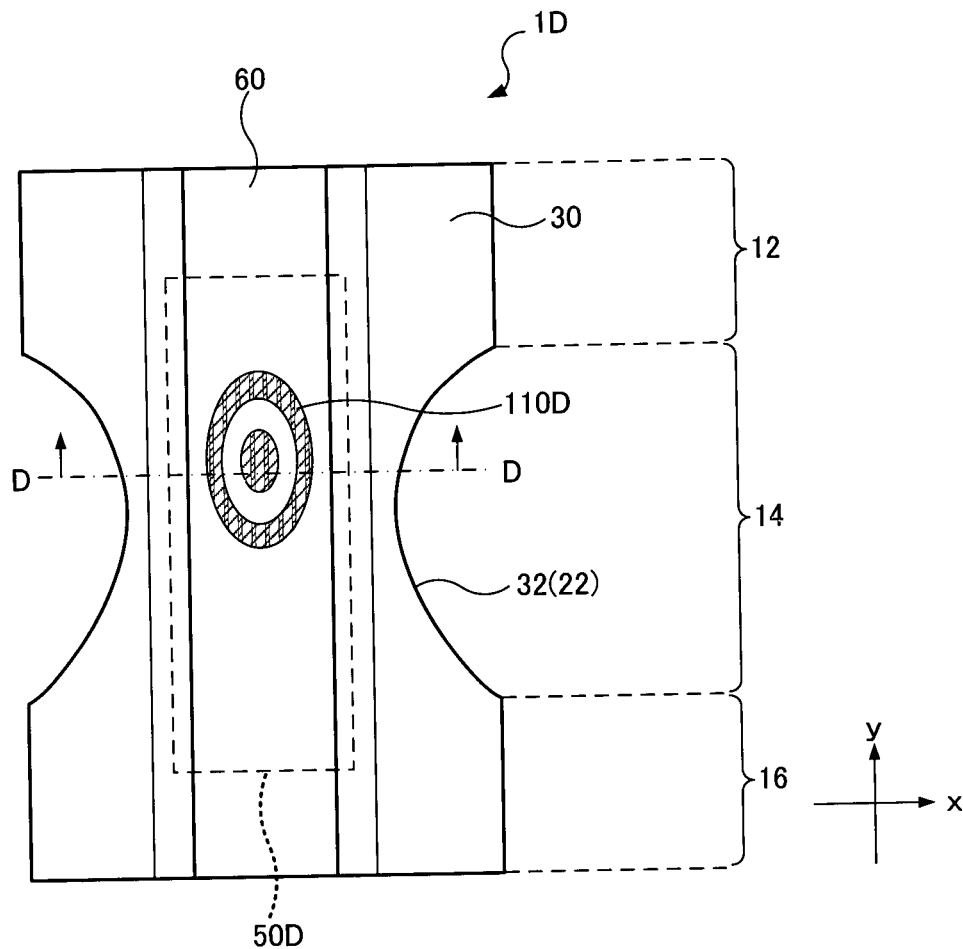
FIG. 6 is a drawing explaining a variation of an absorbent article of the first embodiment of the present invention.
Figure 6:
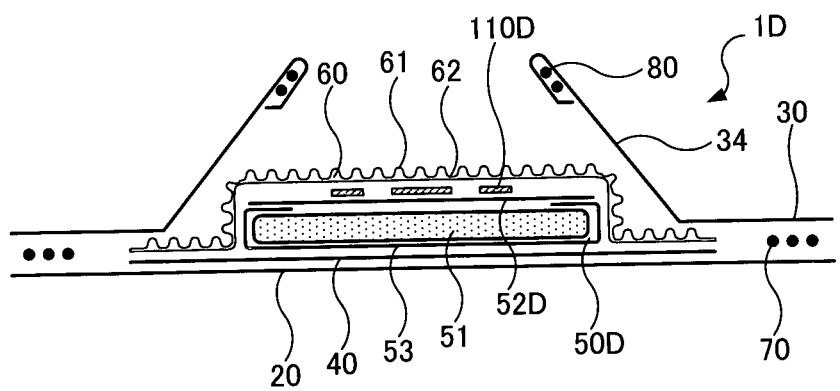

(4) In coloring an upper covering sheet and the second sheet 90B, coloring may also be carried out by printing a prescribed shape or pattern in a color other than white, such as a chromatic color such as blue or green or an achromatic color such as gray, on the surface of the top sheet side of the upper covering sheet or second sheet. For example, as shown in the absorbent article 1D of FIG. 6, an oval shape 110D having a color other than white may be formed by printing on the surface of the top sheet side of an upper covering sheet 52D of an absorbent 50D. Here, FIG. 6(a) is an overhead view of the absorbent article, and FIG. 6(b) is a cross-sectional view taken along line D-D of FIG. 6(a). As a result, a user is able to easily recognize an area, such as an absorption zone, by carrying out printing only in a prescribed area, such as an absorption zone. In addition, since the surface irregularities of the protrusions 61 and the indentations 62 of the skin contact surface of the top sheet 60 are emphasized in a prescribed area, such as an absorption zone, the absorbency of a prescribed area, such as an absorption zone, can impart a strong impression to a user.

(5) A striped pattern that extends in the same direction as the direction in which the protrusions 61 and the indentations 62 of the top sheet 60 extend may be displayed in a region in the center in the widthwise direction of the front torso-surrounding area 12 and/or the rear torso-surrounding area 16 of an absorbent article. For example, as shown in an absorbent article 1E of FIG. 7(a), a striped pattern 130 that extends in the same direction as the direction in which the protrusions 61 and the indentations 62 of the top sheet 60 extend may be formed in an area in the center in the widthwise direction of the rear torso-surrounding area 16 of an absorbent article. As a result, when a user has spread out a disposable diaper in order to put the disposable diaper on a wearer, the user is able to recognize that surface irregularities are present on the skin contact surface of the top sheet 60 in the rear torso-surrounding area 16 before looking at the surface irregularities on the skin contact surface of the top sheet 60 in the crotch area 14. The color of the striped pattern is preferably similar to the color visible through the top sheet in the crotch area 14. For example, in the case the color visible through the top sheet is blue, then the color of the striped pattern is preferably also blue.

Figure 7:
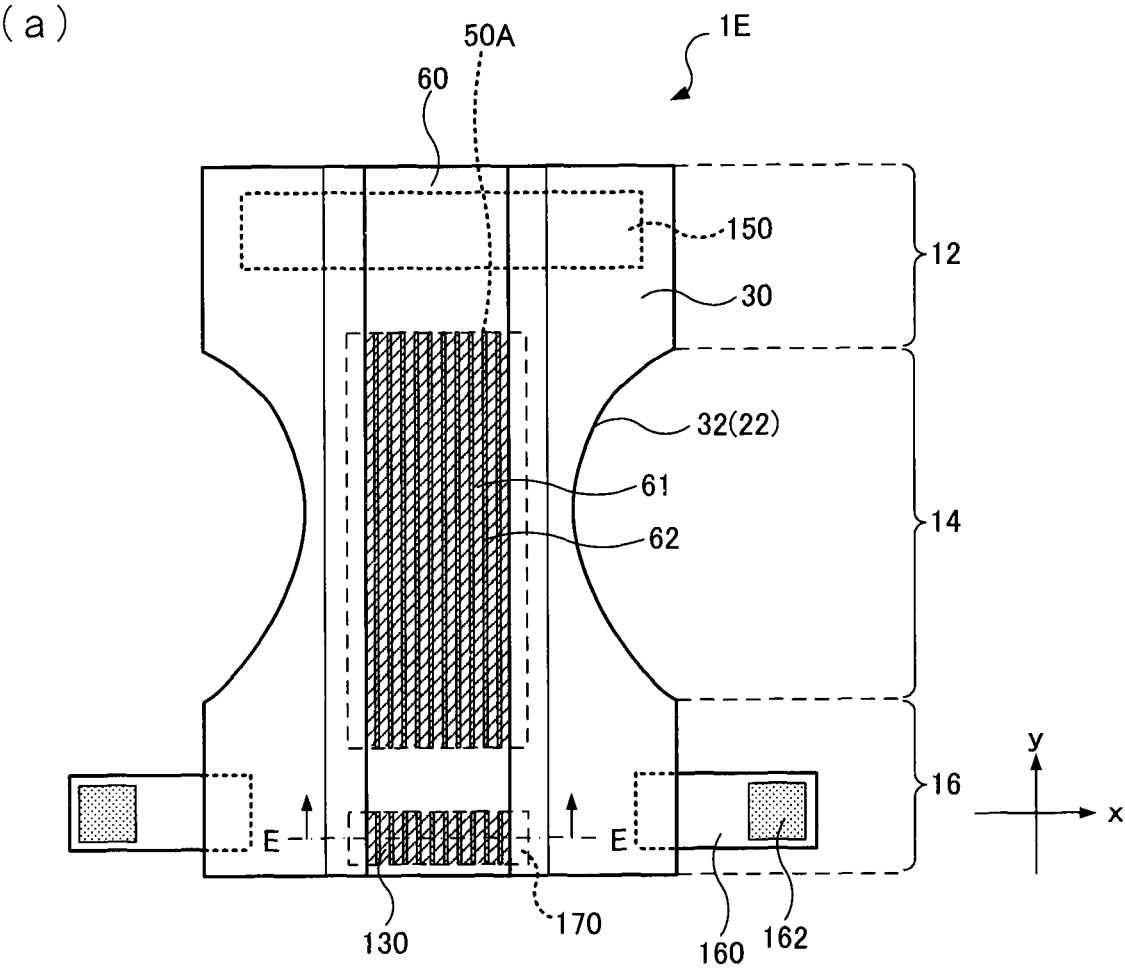
FIG. 7 is a drawing explaining a variation of an embodiment of the present invention.
Figure 7:
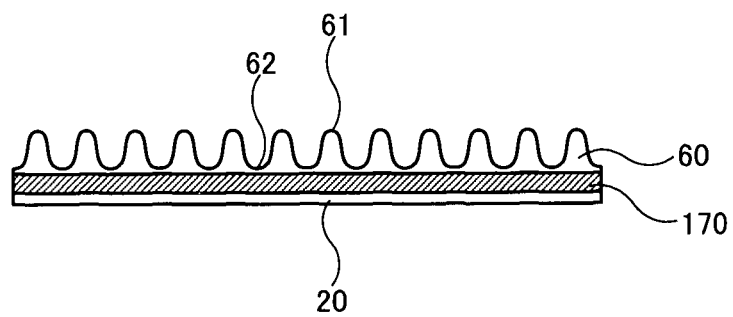

A fastening element 150 is preferably provided on the non-skin contact surface of the front torso-surrounding area 12 of the absorbent article 1E shown in FIG. 7(a), and adhesive tape 160 is provided on both sides in the widthwise direction of the rear torso-surrounding area 16 of the absorbent article 1E. Loops provided on the surface of the fastening element 150 and hooks 162 provided on the distal end of the adhesive tape 160 compose a planar fastener.

FIG. 7(b) is a cross-sectional view taken along line E-E of FIG. 7(a). As shown in FIG. 7(b), a striped pattern 130 can be visible from the skin contact surface side of the top sheet 60, in an area in the center in the widthwise direction of the front torso-surrounding area 12 and the rear torso-surrounding area 16 of the top sheet 60 by providing an elastic member 170 colored to a color other than white. A sheet-like non-woven fabric, urethane sheet or thread-like elastic body arranged in rows to impart elasticity, for example, may be used for the elastic member 170. As a result of the top sheet 60 being contracted in the widthwise direction by the elastic member 170, the indentations 62 having a low basic weight and thickness are preferentially contracted, resulting in a state in which the protrusions 61 are further raised three-dimensionally. Consequently, the surface irregularities of the protrusions 61 and the indentations 62 of the top sheet 60 appear to be emphasized more than in the case of emphasizing the surface irregularities of the protrusions 61 and the indentations 62 of the top sheet 60 using the colored upper covering sheet 52A and the colored second sheet 90B. In addition, although the compressed indentations 62 are stretched in the case of stretching the adhesive tape 160 and spreading out a diaper in order to wear the diaper at the time of use, even thought the top sheet 60 stretches, since the manner in which the color of the colored elastic member 170 appears differs between the protrusions 61 and the indentations 62 of the top sheet 60, the arrangement of the top sheet 60 having surface irregularities can be impressed to a user.

(6) In addition to a disposable diaper, the absorbent article in accordance with some embodiments of the present invention can also be applied to an absorbent article such as a sanitary napkin, incontinence pad or panty liner.

One or more embodiments and variations can be combined. Embodiments and variations can also be combined in any manner.

The aforementioned explanation is only intended to be exemplary, and the present invention is not limited by the aforementioned embodiments and variations.

This application claims the benefit of Japanese Application No. 2010-223309 the entire disclosure of which is incorporated by reference herein.

The first aspect of the present invention described above may be arranged in at least the following items:

An absorbent article, comprising: a liquid-permeable top sheet composed of a white non-woven fabric, a liquid-impermeable back sheet provided at a location opposing the top sheet, and an absorbent provided between the top sheet and the back sheet; wherein, a colored element is further provided on the side of the top sheet that does not contact the skin that is visible through the top sheet and is colored to a color other than white, the top sheet has a plurality of protrusions protruding in the thickness direction and a plurality of indentations indented in the thickness direction, formed by discharging a heated fluid, the basis weight of the protrusions is greater than the basis weight of the indentations, and the color difference between the color of the colored element, as viewed through the protrusions of the top sheet, and the color of the colored element, as viewed through the indentations of the top sheet, is 2.8 or more.

Additionally, the present invention may include the following embodiments:

The colored element may be colored a chromatic color such as blue or green or an achromatic color such as gray.

The colour element may be a solid colour or may be only partially colored.

The color may be applied to a surface of the colored element by printing. The colour may be applied in a pattern. The pattern may be oval shaped.

The color element may have a higher density than the topsheet.

The color difference between the Lab value of the color of the colored element, as viewed through the protrusions of the top sheet and the Lab value of the color of the colored element, as viewed through the indentations of the top sheet may be 10.8 or more.

The thickness of the protrusions is greater than the thickness of the indentations.

The basis weight of side edge regions of the protrusions is greater than the basis weight of the area of the protrusions between the side edge regions.

The color difference between the color of the colored element, as viewed through the indentations of the topsheet, and the color of the colored element, as viewed through the side edge regions of the protrusions, may be greater than the color difference between the color of the colored element, as viewed through the protrusions of the top sheet, and the color of the colored element, as viewed through the indentations of the top sheet.

The color of the colored element, as viewed through the protrusions, is preferably measured at the center in the widthwise direction of the protrusions and the color of the coloured element, as viewed through the indentations, is preferably measured at the center in the widthwise direction of indentations.

The color difference of the colored element, as viewed through the side edge regions of the protrusions, is preferably measured at the center in the widthwise direction of the side edge regions of the protrusions.

The absorbent may have a covering sheet that covers an absorbent member of the absorbent, wherein at least a portion of the covering sheet is colored, and the colored portion of the covering sheet defines the colored element.

A second sheet may be provided between the top sheet and the absorbent, wherein the colored element is the second sheet.

The colored element, defined by the covering sheet or the second sheet respectively, may have a smaller area than the absorbent and cover a portion only of the absorbent.

The covering sheet or the second sheet may be coloured by printing an upper surface of those sheets.

The colored element may be an adhesive for adhering the top sheet to the absorbent, wherein the adhesive is only provided at a location opposing the indentations of the top sheet on the non-skin contact surface of the top sheet, and the width of the area where the adhesive is provided is less than the width of the indentations.

The plurality of protrusions and the plurality of indentations of the top sheet may extend in the lengthwise direction and be alternately arranged in the widthwise direction.

The adhesive may comprise a plurality of bands each extending in the lengthwise direction and spaced from one another in the widthwise direction, each band underlying a respective indentation and being narrower than the band it underlies.

There may be provided an elastic sheet material colored to a color other than white that is provided on the surface of the topsheet that does not contact the skin of the wearer and in a central area of the topsheet in the widthwise direction in a region of the top sheet that surrounds the waist of a wearer.

The absorbent article may comprise a disposable diaper.

BRIEF DESCRIPTION OF THE REFERENCE SYMBOLS 1A-1E Absorbent article
20 Chassis
22 Notched portion
30 Flap
32 Notched portion
40 Back sheet
50A-50D Absorbent
51 Absorbent member
52A-52D,53 Covering sheet
60 Top sheet
61 Protrusion
62 Indentation
70,80 Stretchable material
90B Second sheet
100C Adhesive
130 Striped pattern
170 Elastic member
210 Web
211 Protrusion
212 Indentation
220 Suction drum
230 Discharge unit
231 Fluid

The invention claimed is:

1. An absorbent article, comprising:
a liquid-permeable top sheet comprising a white non-woven fabric;
a liquid-impermeable back sheet provided at a location opposing the top sheet;
an absorbent provided between the top sheet and the back sheet; and
a colored element provided on a non-skin contact surface of the top sheet,
wherein
the colored element is visible through the top sheet, and is colored to a color other than white,
the top sheet has a plurality of protrusions protruding in a thickness direction of the absorbent article and a plurality of indentations indented in the thickness direction, formed by discharging a heated fluid,
a basis weight of the protrusions is greater than a basis weight of the indentations, and
a color difference between (i) a Lab value of the color of the colored element, as viewed through the protrusions of the top sheet, and (ii) the Lab value of the color of the colored element, as viewed through the indentations of the top sheet, is 2.8 or more.

2. The absorbent article according to claim 1, wherein the color difference between the Lab value of the color of the colored element, as viewed through the protrusions of the top sheet, and the Lab value of the color of the colored element, as viewed through the indentations of the top sheet, is 10.8 or more.

3. The absorbent article according to claim 1, wherein a thickness of the protrusions is greater than a thickness of the indentations.

4. The absorbent article according to claim 1, wherein
each of the protrusions includes side edge regions, and a middle area between the side edge regions, and
a basis weight of the side edge regions is greater than a basis weight of the middle area between the side edge regions.

5. The absorbent article according to claim 4, wherein the color difference between the color of the colored element, as viewed through the indentations of the topsheet, and the color of the colored element, as viewed through the side edge regions of the protrusions, is greater than the color difference between the color of the colored element, as viewed through the protrusions of the top sheet, and the color of the colored element, as viewed through the indentations of the top sheet.

6. The absorbent article according to claim 1, wherein
the color of the colored element, as viewed through the protrusions, is measured at the center in the widthwise direction of the protrusions, and
the color of the colored element, as viewed through the indentations, is measured at the center in the widthwise direction of indentations.

7. The absorbent article according to claim 5, wherein the color difference of the colored element, as viewed through the side edge regions of the protrusions, is measured at the center in the widthwise direction of the side edge regions of the protrusions.

8. The absorbent article according to claim 1, wherein
the absorbent has an absorbent member and a covering sheet that covers the absorbent member of the absorbent, and
at least a portion of the covering sheet is a colored portion, the colored element including the colored portion of the covering sheet.

9. The absorbent article according to claim 1, further comprising:
a second sheet provided between the top sheet and the absorbent,
wherein the colored element includes the second sheet.

10. The absorbent article according to claim 8, wherein the colored element, defined by the covering sheet, has a smaller area than the absorbent and covers only a portion of the absorbent.

11. The absorbent article according to claim 1, wherein the colored element includes an adhesive for adhering the top sheet to the absorbent,
the adhesive is provided on the non-skin contact surface of the top sheet in areas that coincide with the indentations of the top sheet, and
the width of the area where the adhesive is provided is less than the width of the indentations.

12. The absorbent article according to claim 1, wherein the plurality of protrusions and the plurality of indentations of the top sheet extend in a lengthwise direction of the absorbent article and are alternately arranged in the widthwise direction.

13. The absorbent article according to claim 11, wherein
the plurality of protrusions and the plurality of indentations of the top sheet extend in a lengthwise direction of the absorbent article and are alternately arranged in the widthwise direction; and
the adhesive comprises a plurality of bands each extending in the lengthwise direction and spaced from one another in the widthwise direction, each band underlying a respective indentation and being narrower than the width of the respective indentation.

14. The absorbent article according to claim 1, comprising an elastic sheet material colored to a color other than white, wherein the elastic sheet material is provided on the non-skin contact surface of the topsheet, in a central area of the topsheet in the widthwise direction, and in a region of the top sheet configured to surround a waist of a wearer.

15. The absorbent article according to claim 1, comprising a disposable diaper.

16. The absorbent article according to claim 14, comprising,
a striped pattern that extends in the same direction as the direction in which the protrusions and the indentations of the top sheet extend,
wherein the striped pattern is formed in the central area of the top sheet in the widthwise direction, and in the region of the top sheet configured to surround the waist of the wearer, and
wherein the striped pattern is of the same color as the color of the colored element.

17. The absorbent article according to claim 9, wherein the second sheet has a basis weight greater than that of the top sheet.

18. The absorbent article according to claim 9, wherein the second sheet is provided in a portion, rather than in an entirety, of an area of the absorbent in a plan view along the thickness direction.

19. The absorbent article according to claim 18, wherein the portion where the second sheet is adapted to correspond to a urination point of a wearer and a surrounding area of the urination point.

20. The absorbent article according to claim 8, wherein
the colored element further includes an adhesive adhering the top sheet to the covering sheet of the absorbent, and
a color difference between a Lab value of a color of the covering sheet visible through the protrusions of the top sheet and a Lab value of a color of the adhesive visible through the indentations of the top sheet is 2.8 or more.

21. A disposable diaper, comprising:
a liquid-permeable top sheet composed of a white non-woven fabric;
a liquid-impermeable back sheet provided at a location opposing the top sheet;
an absorbent provided between the top sheet and the back sheet; and
a second sheet colored to a color other than white and provided between the top sheet and the absorbent,
wherein
the top sheet has a plurality of protrusions protruding in a thickness direction of disposable diaper and a plurality of indentations indented in the thickness direction, formed by discharging a heated fluid,
a basis weight of the protrusions is greater than a basis weight of the indentations,
in a plan view along the thickness direction, the second sheet is provided in a portion of an area of the absorbent,
a color difference between (i) a Lab value of the color of the second sheet visible through the protrusions of the top sheet and (ii) the Lab value of the color of the second sheet visible through the indentations of the top sheet is 2.8 or more, and
in the plan view along the thickness direction, the area where the second sheet is provided differs between a disposable diaper for use by men and that for use by women.

* * * * *